United States Patent [19]
Hansen

[11] Patent Number: 5,851,527
[45] Date of Patent: Dec. 22, 1998

[54] METHOD FOR ANTIBODY TARGETING OF THERAPEUTIC AGENTS

[75] Inventor: Hans John Hansen, Westfield, N.J.

[73] Assignee: Immunomedics, Inc., Morris Plains, N.J.

[21] Appl. No.: 445,110

[22] Filed: May 19, 1995

Related U.S. Application Data

[63] Continuation of Ser. No. 182,623, Apr. 18, 1988, abandoned.

[51] Int. Cl.$^6$ ................................................ A61K 39/395
[52] U.S. Cl. .................................... 424/178.1; 424/178.1; 424/9.1; 424/179.1; 424/181.1; 530/391.1
[58] Field of Search .................................. 424/178.1, 9.1, 424/9.3, 9.341, 9.6, 179.1, 180.1, 181.1, 182.1, 183.1; 530/391.1, 391.3, 391.5, 391.7, 391.9

[56] References Cited

U.S. PATENT DOCUMENTS

| | | | |
|---|---|---|---|
| 3,952,092 | 4/1976 | Bowen et al. | 424/50 |
| 4,241,045 | 12/1980 | Gaafar et al. | 424/1 |
| 4,472,509 | 9/1984 | Gansow et al. | 424/1.1 |
| 4,749,570 | 6/1988 | Poznansky et al. | 424/94.3 |
| 4,762,707 | 8/1988 | Jansen et al. | 424/94.3 |
| 4,975,278 | 12/1990 | Senter et al. | 424/94.3 |

FOREIGN PATENT DOCUMENTS

| | | |
|---|---|---|
| 0 217 577 | 4/1987 | European Pat. Off. . |
| 0 302 473 | 2/1989 | European Pat. Off. . |
| 0 382 411 | 8/1990 | European Pat. Off. . |
| 0 423 747 | 4/1991 | European Pat. Off. . |
| 8 303 679 | 10/1983 | WIPO . |
| 87/05031 | 8/1987 | WIPO . |
| 88/07378 | 10/1988 | WIPO . |
| 89/10140 | 11/1989 | WIPO . |
| 90/07929 | 7/1990 | WIPO . |

OTHER PUBLICATIONS

Suresh et al Methods in Enzymology vol. 121:211–228 1986.

Philpott et al., "Selective Cytotoxicity of Hapten–substituted Cells With An Antibody–Enzyme Conjugate", *The Journal of Immunology*, vol. 111, No. 3, pp. 921–929, (1973).

Philpott et al., "Affinity Cytotoxicity of Tumor Cells With Antibody–Glucose Oxidase Conjugates, Peroxidase, and Arsphenamine", *Cancer Research*, vol. 34:2159–2164, (1974).

Thorpe, P.E., "Antibody Carriers Of Cytotoxic Agents In Cancer Therapy: A Review", *Monoclonal Antibodies '84: Biological and Clinical Applicaitons*, 1985 Editrice Durtis s.r.l., pp. 475–490.

Baldwin, R.W., "Monoclonal Antibodies In Cancer Treatment", *The Lancet*, pp. 603–605, (1986).

Embleton, M.J., "Targeting Of Anti–Cancer Therapeutic Agents By Monoclonal Antibodies", *Biochemical Society Transactions*, vol. 14:393–395 (1986).

*Primary Examiner*—Lila Feisee
*Assistant Examiner*—Julie E Reeves
*Attorney, Agent, or Firm*—Foley & Lardner

[57] ABSTRACT

The targeting capability of an antibody is enhanced using an antibody-enzyme conjugate and a separate soluble substrate-agent conjugate, wherein the targeted enzyme catalyzes the conversion of a soluble substrate, bearing at least one therapeutic or diagnostic agent, to a product comprising the agent, which accumulates at the target site for effective treatment or diagnosis. This method is useful for targeting any type of agent to a site to which an antibody can selectively bind, including use for imaging, e.g., tumors, infectious lesions, fibrin clots, myocardial infarctions, non-cancerous cells, damaged normal cells, atherosclerotic plaque, lymphocyte autoreactive clones, and for therapy, e.g., with drugs, toxins, immune modulators, radioisotopes or antibiotics.

26 Claims, No Drawings

METHOD FOR ANTIBODY TARGETING OF THERAPEUTIC AGENTS

This application is a continuation of application Ser. No. 07/182,623, filed Apr. 18, 1988, now abandoned.

BACKGROUND OF THE INVENTION

The present invention relates to a method for enhancing the targeting capability of an antibody using an antibody-enzyme conjugate and a separate soluble substrate-agent conjugate, wherein the targeted enzyme catalyzes the conversion of a soluble substrate, bearing at least one therapeutic or diagnostic agent, to a product comprising the agent, which accumulates at the target site for effective treatment or diagnosis. The foregoing method is useful for targeting any type of agent to a site to which an antibody can selectively bind, including use for imaging tumors, infectious lesions, fibrin clots, myocardial infarctions, noncancerous cells, damaged normal cells, atherosclerotic plaque, lymphocyte autoreactive clones, and for therapy.

It is well known that antibodies or antibody fragments can be conjugated to radioisotopes, drugs or toxins to target the diagnostic or therapeutic principle to the tumor or lesion site. A major obstacle to using such methods has been the difficulty of loading the antibody with a sufficient amount of the therapeutic or diagnostic agent. A further complication is that overloading the antibody with a therapeutic or diagnostic agent may cause the body to reject and destroy the antibody conjugate.

Conjugation of cytotoxic drugs to antibodies to achieve a targeted therapeutic result is well known. For example, it is known that methotrexate (MTX) can be conjugated to antibodies and some selective cytotoxicity has been observed. It is desirable to enhance the cytotoxicity of such conjugates by increasing the loading of the cytotoxic drug. However, multiple conjugation of individual drug molecules to an antibody eventually reduces its immunoreactivity, the effect being observed when more than about ten drug molecules are loaded.

It has also been proposed that the drug be conjugated to a polymeric carrier, which in turn may be conjugated to an antibody. This has the advantage that larger numbers of drug molecules can be carried to the target site. Use of polylysine as a polymer carrier was reported by Ryser et al., Proc. Natl. Acad. Sci. USA, 75:3867–3870, 1978. These authors found that only about 13 MTX per carrier could be loaded and immunoreactivity was poor. In addition, the high amine content of the polymer, largely in the form of charged ammonium groups, caused the conjugate to stick to normal cells and vitiated the selectivity of the cytotoxic effect.

Rowland, U.S. Pat. No. 4,046,722, discloses an antibody conjugate wherein a plurality of molecules of a cytotoxic agent are covalently bound to a polymer carrier of molecular weight 5,000–500,000, and the loaded carrier is covalently bound to an antibody by random attachment to pendant amine or carboxyl groups. Ghose et al., J. Natl. Cancer Inst., 61:657–676, 1978, discloses other antibody-linked cytotoxic agents useful for cancer therapy. Shih et al., U.S. Pat. No. 4,699,784 discloses site specific attachment of a methotrexate-loaded aminodextran to an antibody.

Targeted neutron-activated radiotherapy is described, e.g., in Goldenberg et al., Proc. Natl. Acad. Sci. USA, 81:560 (1984); Hawthorne et al., J. Med. Chem., 15:449 (1972); and in Goldenberg, U.S. Pat. Nos. 4,332,647, 4,348,376, 4,361,544, 4,468,457, 4,444,744, 4,460,459, and 4,460,561, and in related pending applications U.S. Ser. Nos. 609,607 (filed May 14, 1984) and 633,999 (filed Jul. 24, 1984), the disclosures of all of which are incorporated herein in their entireties by reference.

The aforementioned references disclose, inter alia, methods of incorporating Boron-10-containing addends into antibody conjugates using, e.g., coupling of a carborane (e.g., linked to a phenyldiazonium ion) to an antibody are which suitable for incorporation of a relatively low number of Boron-10 atoms. Typically, between 10 and 120 B-10 atoms have been attached to IgG before the immunoreactivity and yield of recovered product become unacceptably low, using the carborane-phenyldiazonium conjugation procedure. It is desirable to he able to target a large number of B-10 atoms to a tumor site for effective therapy.

A need therefore continues to exist for a method of antibody targeting where it is possible to deposit a sufficient amount of a therapeutic or diagnostic agent at a target site, without overloading the targeting antibody with the agent and thereby losing immunoreactivity and/or inducing an immunogenic response.

OBJECTS OF THE INVENTION

One object of the present invention is to provide a method for enhancing the targeting capabilities of antibodies by amplifying the targeting event.

Another object of the present invention is to provide agents useful for diagnosis and/or treatment of cancer, infectious lesions or other pathological lesions such as myocardial infarctions.

A further object of the present invention is to achieve a high degree of deposit of therapeutic or diagnostic agents at a target site without a need for high loading of the antibody.

Yet another object of the present invention is to provide a method of targeting a sufficiently large number of boron atoms to a target site to function as an efficient therapeutic agent for thermal neutron activated radiotherapy of tumors and pathological lesions, without having to load the boron atoms onto an antibody.

Other objects of the present invention will become more readily apparent to those of ordinary skill in the art in light of the following discussion.

SUMMARY OF THE INVENTION

These and other objects of the invention are achieved by providing a method for targeting a diagnostic and or therapeutic agent to a target site, which comprises the steps of:

(a) injecting a mammal parenterally with an effective amount for targeting and enzyme activity of an antibody-enzyme conjugate, the antibody being reactive with at least one antigen present at the target site; and (b) after a sufficient period of time for the antibody-enzyme conjugate to localize at the target site and substantially clear from the circulatory system of the mammal, injecting the mammal parenterally with an effective amount for deposition at the target site of a soluble substrate-agent conjugate which is capable of transformation by the enzyme to form a product comprising the agent, which accumulates at the target site for effective treatment and/or diagnosis, the substrate-agent conjugate comprising a substrate for the enzyme, conjugated to at least one diagnostic or therapeutic agent, wherein neither the enzyme nor an enzyme having similar activity with respect to the substrate-agent conjugate is endogenous to the mammal at a non-target site along the route of administration or biodistribution of the substrate-agent conjugate in an amount which interferes with targeting and accretion of said agent.

The invention also provides reagents, sterile injectible preparations and kits for use in practicing the foregoing method.

DETAILED DISCUSSION

The prior art discloses the attachment of therapeutic or diagnostic agents directly to an antibody, or to a carrier attached to an antibody. Some of the problems associated with conjugating an agent to the antibody include cross-linking, loss of immunoreactivity, immunogenicity, insufficient loading of the agent on the antibody and inadequate deposition of the agent at the target site. The present invention overcomes these problems by using an antibody-enzyme conjugate and a separate substrate-agent conjugate, which enables the antibody to target the site without having to load the diagnostic or therapeutic agent onto the antibody.

The method for targeting a diagnostic or therapeutic agent to a target site, according to the present invention, can be accomplished by first injecting a mammal parenterally with an effective amount for targeting and enzyme activity of an antibody-enzyme conjugate and waiting a sufficient amount of time for the conjugate to localize at the target site and substantially clear from the circulatory system of the mammal. The next step of the method is injecting the mammal parenterally with an effective amount for deposition at the target site of a soluble substrate-agent conjugate capable of transformation by the enzyme to a product comprising the agent, which accumulates at the target site for effective treatment and diagnosis. The substrate-agent conjugate is a substrate for the enzyme, conjugated to at least one diagnostic or therapeutic agent.

The antibody component of the antibody-enzyme conjugate is the targeting portion, and serves to bind the conjugate selectively to at least one antigen present at the target site. The enzyme component of the conjugate is thereby localized at the target site. Once the non-targeted conjugate substantially clears from the bloodstream, the substrate-agent conjugate is injected. It should not encounter more than a negligible amount of the antibody-enzyme conjugate or similarly acting endogenous enzyme enroute to the target site.

However, when the substrate-agent conjugate reaches the target site, it will be transformed by the enzyme into a product comprising the diagnostic or therapeutic agent. The enzyme can transform many molecules or subunits of substrate-agent conjugate to liberate many molecules of product in a form which will accrete at the target site due to favorable partition between the fluid bathing the target site and the tissue or other antigen-containing medium at the site itself. Thus, the enzyme amplifies the targeting capability of the antibody without the need to conjugate the agent to the targeting antibody and the agent accumulates at the target site and can effect its diagnostic or therapeutic action there.

Unless otherwise noted, use of the term "antibody" herein will be understood to include antibody fragments and thus to be equivalent to the term "antibody/fragment" which is used interchangeably therefor in this discussion. Antibodies can be whole immunoglobulin of any class, e.g., IgG, IgM, IgA, IgD, IgE, or hybrid antibodies with dual or multiple antigen or epitope specificities, or fragments. e.g., $F(ab')_2$, $F(ab)_2$, Fab', Fab and the like, including hybrid fragments.

Antibodies include antiserum preparations, preferably affinity-purified, having a high immunoreactivity, e.g., a binding constant of at least about $10^7$ l/mole, preferably at least about $10^9$ l/mole, a high immunospecificity, e.g., at least about 40%, preferably at least about 60%, more preferably about 70–95%, and a low cross-reactivity with other tissue antigens, e.g., not more than about 30%, preferably not more than about 15% and more preferably not more than about 5%. The antiserum can be affinity purified by conventional procedures, e.g., by binding antigen to a chromatographic column packing, e.g., Sephadex, passing the antiserum through the column, thereby retaining specific antibodies and separating out other immunoglobulins and contaminants, and then recovering purified antibodies by elution with a chaotropic agent, optionally followed by further purification.

Monoclonal antibodies are also suitable for use in the present method, and are preferred because of their high specificities. They are readily prepared by what are now considered conventional procedures of immunization of mammals with an immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present method.

Antibody fragments can be made by pepsin or papain digestion of whole immunoglobulins by conventional methods such as those disclosed, inter alia, in U.S. Pat. No. 4,331,647.

The target sites can be, but are not limited to, cancers, infectious and parasitic lesions, fibrin clots, myocardial infarctions, atherosclerotic plaque, damaged normal cells, non-cancerous cells and lymphocyte autoreactive clones.

Many antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,460,459 and 4,460,561, and in related pending applications U.S. Ser. Nos. 609,607 and 633,999, the disclosures of all of which are incorporated in their entireties herein by reference.

Anti-fibrin antibodies are well known in the art. Antibodies that target myocardial infarctions are disclosed in, e.g., Haber, U.S. Pat. No. 4,036,945, the disclosure of which is incorporated in its entirety herein by reference. Antibodies that target normal tissues or organs are disclosed in, e.g., U.S. Pat. No. 4,735,210, the disclosure of which is incorporated in its entirety herein by reference. Anti-fibrin antibodies are well known in the art, as are antibodies that bind to atherosclerotic plaque and to lymphocyte autoreactive clones.

In general, antibodies can usually be raised to any antigen, using the many conventional techniques now well known in the art. Any targeting antibody to an antigen which is found in sufficient concentration at a site in the body of a mammal which is of diagnostic or therapeutic interest can be used to make the antibody-enzyme conjugate for use in the method of the invention.

It should also be noted that a bispecific antibody/fragment can be used in the present method, with at least one binding site specific to an antigen at a target site and at least one other binding site specific to the enzyme component of the antibody-enzyme conjugate. Such an antibody can bind the enzyme prior to injection, thereby obviating the need to covalently conjugate the enzyme to the antibody, or it can be injected and localized at the target site and, after non-targeted antibody has substantially cleared from the circulatory system of the mammal, enzyme can be injected in an amount and by a route which enables a sufficient amount of the enzyme to reach the localized antibody and bind to it to form the antibody-enzyme conjugate in situ.

Bispecific antibodies can be made by a variety of conventional methods, e.g., disulfide cleavage and reformation of mixtures of whole IgG or, preferably, F(ab')$_2$ fragments, fusions of more than one clone to form polyomas that produce immunoglobulins having more than one specificity, and by genetic engineering. The bispecific antibodies can bind to one or more epitopes on the enzyme but should not bind to a site that interferes with enzyme activity.

The enzyme used in the present invention must be capable of transforming a substantially soluble substrate-agent conjugate to form a product comprising a diagnostic and/or therapeutic agent, which accumulates at the target site. Neither the enzyme nor an enzyme with similar substrate specificity should be endogenous to the mammal along the route of administration or biodistribution of the substrate-agent conjugate. Otherwise, the agent will be released at sites other than the target site, which usually, though not always, will interfere with or compromise the efficacy of the diagnostic or therapeutic effect of the agent.

In principle, the enzyme can be any type of enzyme that can be bound to an antibody and can transform a substrate-agent conjugate to product, subject to the above-mentioned caviats. Proteases, glycosidases, esterases and the like are all general types of enzymes that can be used in the invention under the proper circumstances. More specific examples of suitable enzymes include, but are not limited to, glucuronidase, beta-glucosidase, beta-lactamase, cellulase, dextranase, fructase, aminopeptidase and lysozyme.

The enzyme is selected as a function of the type of substrate-agent conjugate chosen. For example, the choice of dextran as a substrate would be coupled with the use of dextranase as the enzyme. Similarly, cellulase would be used with a cellulose substrate. A glucuronide as the substrate-agent conjugate would be coupled with glucuronidase as the enzyme, and the like.

Apart from the in situ method of forming the antibody-enzyme conjugate, it is advantageous to covalently bind the enzyme to the antibody, directly or through a short or long linker moiety, through one or more functional groups on the antibody and/or the enzyme, e.g., amine, carboxyl, phenyl, thiol or hydroxyl groups. Various conventional linkers can be used, e.g., disiocyanates, diisothiocyanates, bis (hydroxysuccinimide) esters, carbodiimides, maleimide-hydroxysuccinimide esters, glutaraldehyde and the like.

A simple, method is to mix the antibody with the enzyme in the presence of glutaraldehyde to form the antibody-enzyme conjugate. The initial Schiff base linkages can be stabilized, e.g., by borohydride reduction to secondary amines. This method is conventionally used to prepare, e.g., peroxidase-antibody conjugates for immunohistochemical uses or for immunoassays. A diisothiocyanate or a carbodiimide can be used in place of glutaraldehyde.

More selective linkage can be achieved by using a heterobifunctional linker such as a maleimide-hydroxysuccinimide ester. Reaction of the latter with an enzyme will derivatize amine groups on the enzyme, and the derivative can then be reacted with, e.g., an antibody Fab fragment with free sulfhydryl groups (or a larger fragment or intact immunoglobulin with sulfhydryl groups appended thereto by, e.g., Traut's Reagent).

It is advantageous to link the enzyme to a site on the antibody remote from the antigen binding site. This can be accomplished by, e.g., linkage to cleaved interchain sulfhydryl groups, as noted above. Another method involves reacting an antibody whose carbohydrate portion has been oxidized, with an enzyme which has at least one free amine function. This results in an initial Schiff base (imine) linkage, which is preferably stabilized by reduction to a secondary amine, e.g., by borohydride reduction, to form the final conjugate.

Because of the size of the conjugate, it will normally be preferably to link one antibody to one enzyme molecule. However, it may be advantageous to bind a plurality of antibody fragments, e.g., Fab or F(ab')$_2$ fragments, to a single enzyme to increase its binding affinity or efficiency to the antigen target. Alternatively, if the enzyme is not too bulky, it may be useful to link a plurality of enzyme molecules to a single antibody or antibody fragment to increase the turnover number of the conjugate and enhance the rate of deposition of the diagnostic or therapeutic agent at the target site. Conjugates of more than one enzyme and antibody can also be used, provided they can reach the target site and they do not clear too fast. Mixtures of different sized conjugates, or conjugates that contain aggregates can be used, again with the same caveats just noted.

The antibody-enzyme conjugate can be further labeled with, or conjugated or adapted for conjugation to, a radioisotope or magnetic resonance image enhancing agent, to monitor its clearance from the circulatory system of the mammal and make certain that it has sufficiently localized at the target site, prior to the administration of the substrate-agent conjugate. Alternatively, the conjugate can be tagged with a label, e.g., a radiolabel, a fluorescent label or the like, that permits its detection and quantitation in body fluids, e.g., blood and urine, so that targeting and/or clearance can be measured and/or inferred.

Any conventional method of radiolabeling which is suitable for labeling proteins for in vivo use will be generally suitable for labeling antibody-enzyme conjugates, and often also for labeling substrate-agent conjugates, as will be noted below. This can be achieved by direct labeling with, e.g., I-131, I-123, metallation with, e.g., Tc-99m or Cu ions or the like, by conventional techniques, or by attaching a chelator for a radiometal or paramagnetic ion. Such chelators and their modes of attachment to antibodies are well known to the ordinary skilled artisan and are disclosed inter alia in, e.g., the aforementioned Goldenberg patents and in Childs et al., J. Nuc. Med., 26:293 (1985).

The substrate-agent conjugate will include a substrate, which can be transformed by the localized enzyme of the antibody-enzyme conjugate to a product. The agent will be a diagnostic or therapeutic agent whose targeting at a specific site will be advantageous for its efficacy. Such therapeutic and diagnostic agents include, e.g., toxins, antibiotic or chemotherapeutic drugs, radioisotopes, paramagnetic ions, boron addends, cytokines, photosensitizers, radiosensitizers vasodilators and the like.

The substrate-agent conjugate must be soluble, for purposes of administration and transport to the target site. It must also be capable of reaching the target and being transformed to a product which has a substantially more favorable partition coefficient for attraction to the site than the conjugate. As used herein, the term "soluble" means soluble in the fluid into which it is administered and by which it is transported to the target site, to a sufficient extent to permit transport of a diagnostically or therapeutically effective amount of the conjugate to such site. Normally, administration will be into the bloodstream, by intravenous or intraarterial infusion, and the conjugate will need to be soluble in serum and preferably sufficiently hydrophilic to be carried largely by the aqueous phase of serum and diffuse relatively easily through the walls of the blood vessels into interstitial fluid, for cases where such is necessary.

Of course, in the case of cardiac imaging or imaging or therapy of athersclerotic plaque, or the like, where the target site is in the circulatory system, hydrophilic/lipophilic solubility will not be as important as reduction in serum solubility with cleavage of the substrate-agent conjugate by the enzyme to a product which partitions more favorably to the target. It is this partitioning out of the agent, once the substrate-agent conjugate is acted upon by the enzyme component of the targeted antibody-enzyme conjugate, so that the agent then accretes at the target site to a significantly greater extent than the substrate-agent conjugate would accrete in the absence of the enzyme, that characterizes the targeting mechanism of the invention.

This will be better understood in light of some general examples and some more detailed description of various species.

The general method of preparing a substrate-agent conjugate according to the invention involves covalently binding at least one therapeutic or diagnostic agent to a substrate.

Certain cytotoxic drugs that are useful for anticancer therapy are relatively insoluble in serum. Some are also quite toxic in unconjugated form and their toxicity is considerably reduced by conversion to conjugates. Conversion of a relatively poorly soluble drug to a more soluble conjugate, e.g., a glucuronide, will improve its solubility in the aqueous phase of serum and its ability to pass through venous, arterial or capillary cell walls and reach the interstitial fluid bathing the tumor. In fact, conversion of certain toxic substances such as aromatic or alicyclic alcohols, thiols, phenols and amines to glucuronides in the liver is the body's method of detoxifying them and making them more easily excreted in the urine.

The drug is attached to glucuronic acid to form the glucuronide, which solubilizes the conjugate. The attachment is usually to a hydroxyl, thiol or amine function of the drug, which forms an acetal, thioacetal or aminoacetal with the aldehyde carbon of the glucuronic acid. The conjugate can be cleaved at the target site by the enzyme glucuronidase, which would be the enzyme component of the antibody-enzyme conjugate. The free drug would then be rendered significantly less soluble in the interstitial fluid, and would tend to deposit on the cell membrane of surrounding cells and exert its cytotoxic effect at the site of localization of the antibody-enzyme conjugate.

One method of preparing such glucuronides is to inject a mammal, e.g., a cow, goat, horse or primate, with the drug. Some of the drug is converted to glucoronides in the liver of the animal, and the drug-glucuronide conjugate is then excreted in the urine. The drug is preferably administered by slow I.V. infusion, via a liver pump, through the hepatic artery or the portal vein. Collection of the urine and extraction of the glucuronide conjugate can then be effected, e.g., by ion exchange chromatography. An alternative approach is to react UDP-glucuronic acid with the drug and then isolate the glucuronide from the reaction mixture. The reaction can be catalyzed by enzymes isolated from the endoplasmic reticulum of the liver of mammals, and/or the reaction can be carried out in the presence of extracts or tissue homogenates of the endoplasmic reticulum.

One type of antitumor drug that can be converted to such a substrate is epirubicin, a 4'-epimer of doxorubicin (Adriamycin), which is an anthracycline glycoside and has been shown to be a substrate for human beta-D-glucuronidase (Arcamone, Cancer Res., 45:5995, 1985). Other analogues with fewer polar groups would be expected to be more lipophilic and show greater promise for such an approach. Other drugs, toxins, boron compounds or chelators with aromatic or alicyclic alcohol, thiol or amine groups would also be candidates for such conjugate formation.

Another type of substrate-agent conjugate is a polymer with a plurality of agents linked thereto at intervals along the polymer backbone. The polymer can be one that is a substrate for the enzyme component of the antibody-enzyme conjugate or it can have segments or branches that are substrates for such enzyme. The agent molecules are bound to the polymer in such a way that cleavage by the enzyme will liberate the agent, free of polymer units or bound to a small enough number of units to have the requisite lower solubility, or more favorable partition coefficient to cells, tissues, lesion components or the like loci at the target site, relative to the fluid bathing such loci.

Examples of polymers for such use include, e.g., polyols, polysaccharides, polypeptides and the like. One type of polysaccharide is dextran, an alpha-glycoside, which can be cleaved with the enzyme dextranase. The diagnostic or therapeutic agent can be functionalized to contain reactive groups towards the dextran hydroxyls, e.g., anhydrides, isocyanates or isothiocyanates and the like. Alternatively, dextran can be derivatized in a number of ways, e.g., by conversion to an amino-dextran.

The process for preparing a substrate-agent conjugate with an aminodextran (AD) carrier normally starts with a dextran polymer, advantageously a dextran of average molecular weight (MW) of about 10,000–100,000, preferably about 10,000–40,000, and more preferably about 15,000. The dextran is then reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures.

It is convenient to adjust the amount of oxidizing agent so that about 50–150, preferably 100 aldehyde groups are generated, for a dextran of MW of about 40,000, with about the same proportion of aldehyde groups for other MW dextrans. A larger number of aldehyde groups, and subsequent amine groups, is less advantageous because the polymer then behaves more like poylysine and may also be resistant to enzyme cleavage. A lower number results in less than desirable loading of drug, toxin, chelator or boron addend, which may be disadvantageous, especially if the turnover number of the enzyme is low.

The oxidized dextran is then reacted with a polyamine, preferably a diamine, and more preferably a mono- or poly-hydroxy diamine. Suitable amines include, e.g., ethylene diamine, propylene diamine or similar polymethylene diamines, diethylene triamine or like polyamines, 1,3-diamino-2-hydroxypropane or other like hydroxylated diamines or polyamines, and the like. An excess of the amine relative to the aldehyde groups can be used, to insure substantially complete conversion of the aldehyde functions to Schiff base (imine) groups.

Reductive stabilization of the resultant intermediate is effected by reacting the Schiff base intermediate with a reducing agent, e.g., NaBH$_4$, NaBH$_3$CN, or the like. An excess of the reducing agent is used to assure substantially complete reduction of the imine groups to secondary amine groups, and reduction of any unreacted aldehyde groups to hydroxyl groups. The resultant adduct can be further purified by passage through a conventional sizing column to remove cross-linked dextrans. An estimate of the number of available primary amino groups on the AD can be effected by reaction of a weighed sample with trinitrobenzenesulfonic acid and correlation of the optical density at 420 nm with a standard. This method normally results in essentially complete conversion of the calculated number of aldehyde groups to primary amine groups on the AD.

Alternatively, the dextran can be derivatized by conventional methods for introducing amine functions, e.g., by reaction with cyanogen bromide, followed by reaction with a diamine.

The AD should be reacted with a derivative of the particular drug, toxin, chelator or boron addend, in an activated form, preferably a carboxyl-activated derivative, prepared by conventional means, e.g., using dicyclohexylcarbodiimide (DCC) or a water soluble variant thereof.

Methotrexate (MTX) is a typical drug for use in preparing conjugates according to the invention and will be used to illustrate one of the procedures. Analogous steps will be used for other drugs, toxins, chelators and boron addends, modified in appropriate ways which will be readily apparent to the ordinary skilled artisan. Activation of MTX is conveniently effected with any of the conventional carboxyl-activating reagents, e.g., DCC, optionally followed by reaction with N-hydroxysuccinimide (HOSu), to form the active ester. The reaction is normally effected in a polar, aprotic solvent, e.g., dimethylformamide (DMF), dimethylsulfoxide (DMSO) or the like. Other activated esters, e.g., p-nitrobenzoate and the like, can also be used, as can mixed anhydrides. The DCC/HOSu activation is mild and the activated MTX can be reacted in aqueous medium with the AD, so it is preferred.

The proportions of activated MTX to AD are preferably such that about half of the amino groups available on the AD react to form amide bonds with the carboxyl of the activated MTX. Thus, if about 100 amine groups are available on an AD with a starting MW of about 40,000, up to about 50 of these should be reacted with activated MTX. Using a proportion of about 50:1 MTX:AD, about 25–50 MTX molecules are normally introduced. It is difficult to achieve higher loading because of incipient precipitation of the adduct due to the increasing insolubility thereof.

As an illustration of the adaptations to be used for other drugs, loading with 5-flourouracil (5-FU) can be effected by oxidizing 5-flourouridine at the carbohydrate portion, e.g., using periodate, reacting this intermediate with an aminodextran, and reductively stabilizing the Schiff base adduct. Cycloheximide can be loaded by direct reaction of its cyclohexanone carbonyl with aminodextran amine groups, followed by reductive stabilization, or by reacting its side chain hydroxyl with an excess of a diisothiocyanate linker and reaction of the isothiocyanate derivative with amines on the aminodextran, or by reaction of the imide nitrogen with e.g., a haloacid or haloester, followed by activation of the resultant carboxyl derivative, e.g., with DCC, and condensation with amines on the aminodextran.

Another illustration is provided by the antibiotic mitomycin C and its analogues. This molecule has an amine function and a cyclic imine, either of which can be reacted with an alkylating activating group, e.g., succinimidyloxy iodoacetate or sulfosuccinimidyloxy (4-iodoacetyl) aminobezoate (sulfo-SIAB), the resulting intermediate is then used to alkylate amine groups on an aminodextran. Alternatively, carboxyl groups can be introduced using, e.g., succinic anhydride, then activated, e.g., with DCC, and the activated intermediate coupled as before.

Toxins, e.g., pokeweed antiviral protein (PAP) or the ricin A-chain, and the like, can be coupled to aminodextrans by glutaraldehyde condensation or by reaction of activated carboxyl groups on the protein with amines on the aminodextran.

Many drugs and toxins are known which have a cytotoxic effect on tumor cells or microorganisms that may infect a human and cause a lesion, in addition to the specific illustrations given above. They are to be found in compendia of drugs and toxins, such as the Merck Index and the like. Any such drug can be loaded onto an AD by conventional means well known in the art, and illustrated by analogy to those described above. The ability to partially or completely detoxify a drug as a conjugate according to the invention, while it is in circulation, can reduce systemic side effects of the drug and permit its use when systemic administration of the unconjugated drug would be unacceptable. For example, MTX and cycloheximide often are too toxic when administered systemically. Administration of more molecules of the drug conjugated to a substrate carrier, according to the present invention, permits therapy while mitigating systemic toxicity.

Loading of drugs on the substrate carrier will depend upon the solubility (partition coefficient between the fluid bathing a target site and the target cells, tissues or other structures, e.g., atherosclerotic plaque, fibrin clot, virus particle, parasite and the like), and upon the efficiency of enzyme cleavage of substrate molecules or subunits to liberate a product comprising the drug which has a sufficiently favorable partition coefficient to the target to effect the desired therapeutic action. In general, it will be desirable to load a drug onto a dextran in a ratio of monosaccharide subunits to drug of from about 3 to about 25, although these are preferred and not limiting amounts. Very heavy loading of drug molecules can inhibit enzyme activity due primarily to steric hindrance to binding of the substrate conjugate to the active site of the enzyme. Too light loading can result in insufficient reduction in fluid solubility for the drug as a result of enzyme cleavage since a smaller portion of the polysaccharide-drug conjugate might diffuse away from the bound enzyme before enough sugar subunits are cleaved off to reduce solubility enough for the drug (with perhaps a few glycoside subunits still bound to it) to be favorably partitioned out of the surrounding fluid to accrete at the target site, e.g., on a tumor cell membrane, on a bacterial cell wall, on an atherosclerotic plaque or a fibrin clot and the like. Toxins may be less heavily loaded than drugs, since they are often larger proteins.

Chelators for radiometals or magnetic resonance enhancers are also well known in the art. Typical are derivatives of ethylenediaminetetraacetic acid (EDTA) and diethylenetriaminepentaacetic acid (DPTA). These typically have groups on the side chain by which the chelator can be attached to a carrier. This same group can be used to couple the chelator to amine groups on an AD. Alternatively, carboxyl or amine groups on a chelator can be coupled to an AD activation or prior derivatization and then coupling, all by well known methods. For example, deferoxamine, which is a chelator for Ga-67, has a free amine group that can be activated with a suitable linker to contain an activated carboxyl, isothiocyanate or like group, and then coupled to amines on an AD.

Other methods of linking chelators to amines of an AD will be apparent to the skilled artisan, depending on the functionality of the chelator.

Boron addends, e.g., carboranes, when attached to the substrate conjugate and targeted by the antibody to lesions, can be activated by thermal neutron irradiation and converted to radioactive atoms which decay by alpha emission to produce highly cytotoxic short-range effects. High loading of boron addends, as well as magnetic resonance enhancing ions, is of great importance in potentiating their effects. Carboranes can be made with carboxyl functions on pendant side chains, as is well known in the art. Attachment of these carboranes to AD's by activation of the carboxyl groups and condensation with amines on the carriers enables preparation of useful substrate-agent conjugates.

In one embodiment of the present invention, the substrate-agent conjugate would contain a large number of boron atoms, more preferably prepared from reagents enriched in Boron-10 isotope, boron containing reagents enriched to about 96% Boron-10 being commercially available. Such a conjugate would be of great utility in neutron activated radiotherapy, since it could bring to a tumor site or the site of a pathological lesion a sufficient number of boron atoms to provide a therapeutic dosage of alpha particles to the targeted tissue upon thermal neutron irradiation, even when the percentage of an injected dose of antibody-enzyme conjugate which localizes in the target tissue is relatively low, e.g., 1–10%. Such localization percentages are not uncommon for antibody-targeted species.

The boron-loaded substrate conjugates according to the present invention have a number of boron atoms per substrate molecule normally ranging from at least about 50 up to about 10,000, preferably from about 200 to about 2,000. To reiterate, these are preferably about 96% Boron-10 enriched, although it may he more cost effective to use a conjugate having a larger number of boron atoms with the 20% natural abundance of Boron-10 isotope.

The substrate-agent conjugate can contain moieties which do not contain boron, or which contain boron and other useful functions. e.g., a radionuclide, especially I-123, I-125 or I-131, or functions such as chelators, chelates with metal ions, drugs, toxins, chromophores, chromogens, fluorescent markers, and the like, all of which can contribute to the therapeutic effect thereof, or permit monitoring of deposit and/or clearance of the boron addend, or provide complementary therapeutic activity. The substrate-agent conjugate may incorporate functions whose primary purpose is to improve the lipid solubility and decrease the water solubility of the resultant enzyme cleavage product containing the boron addend.

It is useful to employ boron cage compounds to make such conjugates, because of their relative ease of handling and the fact that each such cage compound can carry 5–12 boron atoms to the target site. The most common and readily available kinds of boron cage compounds are the carboranes. The skilled artisan will be aware of general references in the field for most of the reactions to be discussed hereinafter, the best and most comprehensive references being Muetterties et al., "Polyhedral Boranes", (Dekker, New York, 1968); Muetterties, Ed., "Boron Hydride Chemistry", (Academic Press, New York, 1975); and Grimes, "Carboranes", (Academic Press, New York, 1970). These references contain copious bibliographies on specific topics within the broad subject range of synthesis of organic derivatives containing a plurality of boron atoms. Hawthorne. U.S. patent application Ser. No. 742,436, filed Jun. 7, 1985, is replete with such details, and this application is incorporated in its entirety herein by reference.

An alternative to an alpha-glycoside such as dextran or amino-dextran is a beta-glycoside such as carboxymethylcellulose (CMC), which can be cleared by a cellulase enzyme. Attachment of diagnostic or therapeutic agents to the CMC will be analogous to the method used for dextran, since both are sugar polymers, differing only in the stereochemistry of the glycosidic linkage. Derivatization of the CMC to append functional molecules is perhaps most conveniently accomplished by reacting it with a carbodiimide type of condensing agent and using an amine function on the diagnostic or therapeutic agent to form amide linkages. Alternatively, mild oxidation with glycol cleavage reagents, e.g., periodate, to form aldehyde groups at a plurality of points along the polymer chain, followed by reaction with a diamine, will form an aminoCMC suitable for reaction with a variety of different functional groups. Condensation of the oxidized CMC with amines and borohydride stabilization is also practicable. Other means of attachment of agents to the CMC will be readily apparent to the ordinary skilled artisan.

Yet another variant on the polymer substrate is a polymer that is not cleaved by the enzyme, but which bears short linker segments of an oligomer that is a substrate for the enzyme, and which bears drugs, chelators, boron addends and like diagnostic or therapeutic agents. As one illustration, a polyvinyl alcohol could be used as a carrier for a plurality of short oligosaccharides, e.g., short dextran or cellulose oligomers of, e.g., 5–50, preferably 5–20, glycoside subunits. The polyvinyl alcohol could be aminated by, e.g., cyanogen bromide followed by diamine condensation. The oligosaccharide could be mildly oxidized with, e.g., periodate, and condensed with the aminated polymer to form Schiff base linkages, which are preferably further stabilized by borohydride reduction. The resultant oligomer-charged polymer can then be lightly aminated as described earlier for dextran or cellulose polymers, or otherwise conventionally functionalized, to put at least 2, preferably about 2–5 amine groups on each of the oligomer linkers. An average of about 1–3 drug molecules, chelators, boron addends or other agents is then conjugated to each of the oligomers.

It will be reaidly apparent that many other variants can be envisioned. The condensation of the lightly oxidized dextran oligomer linkers to the aminated polymer and the drug or other agent can be effected simultaneously or sequentially and stabilized later. Other functional groups on the agents can be used to bind to the oligomer, and other functional groups can be used to bind the oligomer to the polymer carrier.

An acrylate polymer can be used, with aminodextran oligomers bound to it by amide linkages formed by carbodiimide activation of the acrylate carboxyls. A polypeptide can be used, with the oligomer linkers attached to carboxyl or amine residues on the carrier. A short polyester or oligopeptide linker can be used instead of an oligosaccharide linker, with an esterase or peptidase enzyme that cleaves the linker. The ordinary skilled artisan will be able to envision other variants that fall within the broad scope of the invention and can be prepared by conventional synthetic methods.

Still another approach is to use a carrier polymer that bears the drugs, chelators, boron addends or other agents and that has a high attraction for the target, in unmodified form, but which is then modified by conjugation to solubilizing substrate molecules which are then cleaved by targeted enzyme. One illustration of this subgeneric type of substrate-agent conjugate is a polylysine to which are bound a plurality of radiometal or paramagnetic metal chelators, carboranes or MTX molecules. This carrier conjugate is then condensed with a plurality of short dextran oligomers, e.g., by Schiff base formation with lightly oxidized dextran and borohydride stabilization, in a ratio which increases the solubility (reduces the "stickiness") of the polylysine and makes it readily transportable in serum and readily diffusable through capillary walls (and then loaded with radioisotope or paramagnetic ions, if chelators are attached to the carrier). At a target site, e.g., a tumor, a localized antitumor antibody-dextranase conjugate would strip off the dextran coating from the polylysine to a sufficient extent to make it "sticky" again, whereupon it would adhere to the tumor cells and the bound polylysine, bearing its loading of diagnostic or therapeutic agent would then act upon the tumor cell to permit imaging or cytotoxic therapy.

A heavily aminated aminodextran can function as a polylysine, and can be substituted with short oligomeric substrate linkers as discussed above. It will be "sticky" towards cell membranes and other tissues in a similar fashion to polylysine. Other polypeptides or heavily aminated polymers can function in analogous fashion as carriers for substrate coating and solubilization. In fact, amination is not essential to the loaded carrier function, since any functionality that causes favorable partitioning out of a conjugate of a carrier and one or more diagnostic and/or therapeutic agents can be masked by solubilizing substrate oligomers or even small substrate molecules, such that the resultant more soluble conjugate circulates easily in serum or another fluid for administration and becomes less soluble in the fluid bathing the target site after the coating molecules are cleaved by action of the localized enzyme of the antibody-enzyme conjugate.

The proportions of loaded carrier polymer to "coating" solubilizing substrate groups or oligomers will depend on the nature of the target site and the characteristics of the components. If a polylysine or functional equivalent is used as the carrier, coating with oligodextran will advantageously be effected in a dextran:polylysine ratio of about 1:10 to about 100:1 by weight, preferably about 1:1 to about 10:1, more preferably about 3:1 to about 7:1. An example is a polylysine of MW about 1,500 daltons, coated with about 3–7 dextran oligomers of MW about 15,000 daltons each.

It will be appreciated that clearance of the antibody-enzyme conjugate and/or the substrate-enzyme conjugate can be accelerated, after a sufficient time for localization or deposit of the diagnostic or therapeutic agent, by using a second antibody to complex the conjugate and enhance its rate of uptake by macrophage or the reticuloendothelial system, as disclosed, e.g., in Goldenberg, U.S. Pat. No. 4,624,846. The optimal time for such second antibody clearance can be determined with the aid of a label on either conjugate, so that the extent of localization of the antibody-enzyme conjugate at the target site and/or the extent of deposit of the agent at the target site, and the biodistribution of non-targeted conjugates can be monitored.

The reagents are conveniently provided as dual injectable preparations for human therapeutic and diagnostic use. The first injectable preparation contains an effective amount of an antibody or antibody fragment conjugated to an enzyme, in a pharmaceutically acceptable injection vehicle, preferably phosphate-buffered saline (PBS) at physiological pH and concentration. The second injectable preparation contains an effective amount of a soluble substrate conjugated to at least one diagnostic or therapeutic agent, in a pharmaceutically acceptable injection vehicle, generally similar to that used for the first preparation. The injectable preparations preferably will be sterile, especially if they are intended for use in humans.

The reagents also can be conveniently provided in a therapeutic or diagnostic kit for antibody targeting to a target site, using two suitable containers. The first container has an effective amount of an antibody or antibody fragment covalently bound to an enzyme. The second container has an effective amount of a soluble substrate conjugated to at least one therapeutic or diagnostic agent. The reagents can be lyophilized for longer shelf stability or provided in the form of solutions, optionally containing conventional preservatives, stabilizers and the like. Other optional components of such kits would normally be containers of buffers, labeling reagents, radioisotopes, paramagnetic compounds, second antibody for enhanced clearance, and conventional syringes, columns, vials and the like.

The method of the invention is normally practiced by parenteral injection. The various types of parenteral injections can be, but are not limited to intracavitary (e.g., intraperitoneal), intravenous, intraarterial, intrapleural, intrathecal, intramuscular, intralymphatic and regional intraarterial, intralesional, subcutaneous, catheter perfusion and the like.

For cancer imaging and/or therapy, intravenous, intraarterial or intrapleural administration is normally used for lung, breast, and leukemic tumors. Intraperitoneal administration is advantageous for ovarian tumors. Intrathecal administration is advantageous for brain tumors and leukemia. Subcutaneous administration is advantageous for Hodgkin's disease, lymphoma and breast carcinoma. Catheter perfusion is useful for metastatic lung, breast or germ cell carcinomas of the liver. Intralesional administration is useful for lung and breast lesions.

The above illustrates the general methods of administration of antibody-enzyme conjugates and substrate-therapeutic or diagnostic agent conjugates according to the present invention. It will be appreciated that the modes of administration of the two different conjugates may not be the same, since the clearance pathways and biodistributions of the conjugates will generally differ. For example, intraperitoneal administration of an antibody-enzyme conjugate may be advantageous for targeting an ovarian tumor, whereas intravenous administration of a radioisotope-substrate conjugate for imaging may be desirable because of better control of the rate of deposit and ease of monitoring of the clearance rate.

The antibody-enzyme conjugate will generally be administered as an aqueous solution in PBS, preferably a sterile solution, especially if it is for use in humans. Advantageously, dosage units of about 50 micrograms to about 5 mg of the antibody-enzyme conjugate will be administered, either in a single dose or in divided doses, although smaller or larger doses may be indicated in particular cases. It may be necessary to reduce the dosage and/or use antibodies from other species and/or hypoallergenic antibodies, e.g., fragments or hybrid human or primate antibodies, to reduce patient sensitivity, especially for therapy and especially if repeated administrations are indicated for a therapy course or for additional diagnostic procedures. An indication of the need for such cautionary procedures is an increase in human anti-mouse antibody (HAMA) production, which can be determined using an immunoassay.

It usually takes from about 2 to 14 days and preferably 5 to 14 days for IgG antibody to localize at the target site and substantially clear from the circulatory system of the mammal prior to administration of the substrate-agent conjugate. The corresponding localization and clearance time for F(ab)$_2$ and F(ab')$_2$ antibody fragments is from about 2 to 7 days and preferably 4 to 7 days, and from about 1 to 3 days and preferably 3 days for Fab and Fab' antibody fragments. Other antibodies may require different time frames to localize at the target site, and the above time frames may be affected by the presence of the conjugated enzyme. Again, it is noted that labeling the antibody-enzyme conjugate permits monitoring of localization and clearance.

IgG is normally metabolized in the liver and, to a lesser extent, in the digestive system. F(ab)$_2$ and F(ab')$_2$ are normally metabolized primarily in the kidney, but can also be metabolized in the liver and the digestive system. Fab and Fab' are normally metabolized primarily in the kidney, but can also be metabolized in the liver and the digestive system.

Normally, it will be necessary for at least about 0.0001% of the injected dose of antibody-enzyme conjugate to localize at the target site prior to administration of the substrate-agent conjugate. To the extent that a higher targeting efficiency for this conjugate is achieved, this percentage can be greater, and a reduced dosage can be administered.

It follows that an effective amount of an antibody-enzyme conjugate is that amount sufficient to target the conjugate to the antigen at the target site and thereby bind an amount of the enzyme sufficient to transform enough of the soluble substrate-agent conjugate to product to result in accretion of an effective diagnostic or therapeutic amount of the agent at the target site.

The substrate-therapeutic or diagnostic agent conjugate will be generally administered as an aqueous solution in PBS. Again, this will be a sterile solution if intended for human use. The substrate-agent conjugate will be administered after a sufficient time has passed for the antibody-enzyme conjugate to localized at the target site and substantially clear from the circulatory system of the mammal.

Conjugates of boron addend-loaded carrier for thermal neutron activation therapy will normally be effected in similar ways, and it will be advantageous to wait until non-targeted substrate-agent conjugate clears before neutron irradiation is performed. Such clearance can be accelerated by use of second antibody, as is known from, e.g., U.S. Pat. No. 4,624,846.

An effective amount of a substrate-agent conjugate is that amount sufficient to deliver an effective amount of the agent to the target site and that amount of a substrate which will be capable of transformation by the enzyme to a form of the product that tends to accumulate at the target site. An effective amount of a therapeutic or diagnostic agent is that amount sufficient to treat or diagnose the target site.

If scintigraphic imaging is to be effected, the substrate agent conjugate will include a radiolabeled species bound to a substrate. This can be a chelate of a radiometal or a directly iodinated or metallated compound. Suitable gamma-emitting isotopes include I-131, I-123, Tc-99m, In-111 and Ga-67. The antibody will be one that binds to an antigen at the target site, and the enzyme will be one that converts the substrate-agent conjugate to a product that accretes at the target site in an amount sufficient to permit imaging. Once enough isotope has deposited at the target site, scanning is effected with either a conventional planar and/or SPECT gamma camera, or by use of a hand held gamma probe used externally or internally to localize the tumor, microbiological site of infection, myocardial infarct, atherosclerotic plaque or other target site. The scintigram is normally taken by a gamma imaging camera having one or more windows for detection of energies in the 50–500 keV range. Use of radioisotopes with high energy beta or positron emissions would entail use of imaging cameras with the appropriate detectors, all of which are conventional in the art.

As an example, a polylysine oligomer can be conjugated to a plurality of aminomethyl-DTPA chelators, using a succinimidyl p-isothiocyanatobenzoate linker (U.S. Pat. No. 4,680,338), the resultant compound can then be reacted with a plurality of mildly oxidized dextran oligomers, which are then stabilized with borohydride. A patient, e.g., a cancer patient is injected with a conjugate of an antitumor antibody and a dextranase enzyme and 7 days are taken for localization of the conjugate and clearance of non-targeted conjugate. The substrate-chelator conjugate is then charged with Indium-111 ions, sterile filtered in PBS, and injected into the patient. Accretion of the label is seen within about 3 hours, and clearance of background label is substantially complete after about 12–24 hours, at which time imaging is effected.

Magnetic resonance imaging (MRI) is effected in an analogous method to scintigraphic imaging except that the imaging agents will contain MRI enhancing species rather than radioisotopes. It will be appreciated that the magnetic resonance phenomenon operates on a different principle from scintigraphy. Normally the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to increase both $T_1$ and $T_2$, the former resulting in greater contrast, while the latter results in lesser contrast. Accordingly, the phenomenon is concentration-dependent, and there is normally an optimum concentration of a paramagnetic species for maximum efficacy. This optimum concentration will vary with the particular agent used, the locus of imaging, the mode of imaging, i.e., spin-echo, saturation-recovery, inversion-recovery and for various other strongly $T_1$ dependent or $T_2$ dependent imaging techniques, and the composition of the medium in which the agent is dissolved or suspended. These factors, and their relative importance are known in the art. See, e.g., Pykett, Scientific American, 246:78 (1982); Runge et al., Am. J. Radiol., 141:1209 (1987).

Examples of compounds useful for MRI image enhancement include paramagnetic Gd(III), Eu(III), Dy(III), Pr(III), Pa(IV), Mn(II), Cr(III), Co(III), Fe(III), Cu(II), Ni(II), Ti(III) and V(IV) ions, or radicals, e.g., nitroxides, and these would be conjugated to a substrate bearing paramagnetic ion chelators for the ions or linkers for the radical addends. The mr image enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in Pykett, op. cit., and Runge et al., op. cit.

For magnetic resonance imaging (MRI), a similar procedure is used to that used for scintigraphy. In the previous example, because it is desirable to carry a large number of paramagnetic ions to a target site for high contrast MRI enhancement, the polylysine will be loaded with a higher amount of chelators and more of the antibody-enzyme conjugate and the substrate-chelate conjugate will be administered in order to deposit a high concentration of paramagnetic ions at the target site.

The therapeutic method of the invention can be accomplished by conjugating an effective therapeutic amount of a radioisotope such as Y-90 or I-131 (which may be used for both localization and therapy depending on the amount injected) or a drug such as adriamycin for cancer or gentamycin for infection, an immunomodulatory substance such as poly-IC, or a biological toxin such as pokeweed mitogen to the substrate, and depositing a therapeutically effective amount of the agent at the target site. The therapeutic method of the invention can also be accomplished by conjugating one or more boron-10 addends to the substrate and, once the boron-10 is deposited at the target site, e.g., a tumor, effecting external thermal neutron irradiation to the tumor to destroy the neoplastic cells. The boron-10 conjugate may be labeled with a radioisotope chelate to make certain that sufficient boron addends have localized at the target site and that substantially all of the non-targeted boron-10 has left the circulatory system prior to neutron irradiation.

Dosage units of substrate-agent conjugate will depend upon many factors, each of which can be determined in a relatively straightforward manner, so that optimal dosimetry can be effected. It will be helpful, in the initial dosimetric evaluation, to use a radiolabeled substrate-agent conjugate (if the agent is not itself a radioactive isotope) to determine the degree and rate of deposit of the agent at the target site, and the rate of clearance and biodistribution of non-targeted conjugate. Use of a labeled antibody-enzyme conjugate to estimate the amount of enzyme localized at the target site will also aid in dosimetric analysis.

It may be necessary to perform trials for dosimetry, generally using an animal model first, if available, then in a series of patient studies, to optimize the dose of substrate-agent conjugate, as a function of accessibility of the site, mode of administration, turnover number of the enzyme, desired dose of the agent to the site, and rate of clearance of non-targeted conjugate. This will be expected and the techniques for optimization will be within the ordinary skill of the clinician.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of Methotrexate/aminodextran Conjugate (a) Activation of Methotrexate In a dried Reacti-vial, 45.4 mg of methotrexate (0.1 mmole, Sigma) in 1 ml anhydrous DMF is introduced by syringe. A solution of N-hydroxysuccinimide (23 m, 0.2 mmole, Sigma) in 7590 ul of anh. DMf and a solution of 1,3-dicyclohexylcarbodiimide (41.5 mg, 0.2 mmole, Sigma) in 750 ul of anh. DMF are followed. The reaction mixture is stirred in the dark at room temperature for 16 hours under anhydrous conditions. The white precipitate is centrifuged and the clear solution is stored in a sealed bottle at −20° C.

(b) Reaction with Aminodextran

Aminodextran (10 mg, 2.5×10$^4$ mole) is dissolved in 2 ml of PBS, pH 7.2. Activated MTX (125×10$^4$ mmole) is added gradually. The solution is stirred at room temperature for 5 hours and purified by Sephadex G-25 column. The void volume is collected and further dialyzed against reaction buffer. After lyophilization, 2.1 mg of product is obtained (21% yield). The methotrexate incorporation is determined by the absorption at 370 nm to be 38 Methotrexate/dextran.

EXAMPLE 2

Preparation of Chelator-polylysine/dextran Conjugate

Polylysine (MW 15,000) is reacted with an amount of the succinimidyl p-isothiocyanatobenzoate derivative of aminomethyl-DTPA (a succinimidyl benzoate with a thiourea linkage to the DTPA) sufficient to attach an average of 5 DTPA's to the polylysine. The resultant product is reacted with dextran oligomer (MW 1,500) which has been lightly oxidized with periodate to an extent sufficient to produce about 2 aldehyde groups per dextran, in an amount sufficient to load about 3–5 dextran units on the polylysine-DTPA, then stabilized with borohydride to reduce the Schiff base linkages and residual aldehyde groups.

EXAMPLE 3

Preparation of Epirubicin-glucuronide Conjugate

Epirubicin is injected intravenously into a horse over a period of several weeks. Urine is collected, and epirubicin glucuronide is isolated by ion-exchange chromatography of the urine, and purified by further column chromatography and/or HPLC.

EXAMPLE 4

Preparation of Antibody-enzyme Conjugate (A) A substantially monoconjugated enzyme-antibody preparation is prepared by mildly oxidizing the carbohydrate portion of an anti-CEA IgG with periodate, then contacting the oxidized IgG with a dilute solution of dextranase (from Penicillium sp., Worthington Biochemical Corp., Freehold, N.J.) to produce an antibody-enzyme conjugate, which is then stabilized by borohydride, in the usual manner. The conjugate can be radiolabeled with I-131, by conventional procedures.

(B) In a similar fashion to the above Part A, an anti-leukemia IgG is conjugated to glucuronidase (from bovine liver, Worthingon).

EXAMPLE 5

Therapy of Lung Cancer

A human patient having small-cell carcinoma of the right lung is in fused intravenously with a sterile, pyrogen-free solution containing 5 mg of the anti-CEA IgG/dextranase conjugate in PBS, prepared according to Example 4(A) hereof, and labeled with I-131. After 5 days, the conjugate is well localized in the lung and has substantially cleared from the circulation of the patient, as seen by scintigraphic scanning at daily intervals.

A sterile, pyrogen-free PBS solution of the MTX/aminodextran conjugate, prepared according to Example 1, and containing 50 mg of the conjugate, is infused intravenously on each of the next 4 days. Subsequent radioimmunodetection, with I-123-anti-CEA Fab shows significant tumor reduction.

EXAMPLE 6

Therapy of Lymphoma

A human patient suffering from lymphoma is infused intravenously with a sterile, pyrogen-free PBS solution containing 5 mg of the anti-lymphoma IgG-glucuronidase conjugate prepared according to Example 4(b) hereof, labeled with I-131. After 6 days, the conjugate is well localized at the target site and substantially cleared from the circulatory system, as determined by gamma scanning.

The patient is then infused intravenously with a sterile, pyrogen-free PBS solution containing 10 mg of epirubicin glucuronide, prepared according to Example 3 hereof, on each of the next 4 days. Subsequent radioimmunodetection shows significant reduction in the lymphoma.

EXAMPLE 7

Tumor Radioimmunodetection

A human patient with colon cancer is infused intravenously with a sterile, pyrogen-free PBS solution containing 5 mg of the anti-CEA-IgG/dextranase conjugate prepared according to Example 4(A) hereof. After 7 days, the patient is infused intravenously with a sterile, pyrogen-free PBS solution containing 5 mCi of the In-111-labeled polylysine-DTPA/dextran conjugate prepared according to Example 2 hereof and loaded with In-111. After 24 hours, sufficient accretion of the radioisotope at the tumor site occurs for scintigraphic imaging.

EXAMPLE 8

MRI Imaging of Cancer

A human patient having tumor of the ascending colon is infused intravenously with a sterile, pyrogen-free PBS solution containing 5 mg of the anti-CEA-IgG/dextranase conjugate prepared according to Example 4(A) hereof. After 7 days, the patient is infused intravenously with a sterile, pyrogen-free PBS solution containing 500 mg of the Gd(III) loaded polylysine-DTPA/dextran conjugate prepared according to Example 2 hereof. After another 2 days, MRI imaging is effected, revealing an image of the tumor which is adequately distinguished from surrounding tissues.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for targeting a cytotoxic agent to a target site, comprising the steps of:
   (a) injecting a mammal parenterally with an effective amount for targeting of a bispecific antibody or antibody fragment having a first binding site specific for an antigen present at a target site and a second binding site specific for an epitope on an enzyme, wherein binding to said epitope does not interfere with enzyme activity;
   (b) subsequently injecting said mammal parenterally with an effective amount for enzyme activity of said enzyme, such that said bispecific antibody or antibody fragment binds said enzyme to form an antibody-enzyme conjugate in situ; and
   (c) after a sufficient period of time for localization of said antibody-enzyme conjugate at the target site and for unbound antibody-enzyme conjugate to clear from the circulatory system of the mammal, further injecting said mammal parenterally with an effective amount for deposition at said site of a serum soluble polymer substrate-agent conjugate which is capable of transformation by said enzyme to form a product comprising a cytotoxic agent that is relatively insoluble in serum in vivo, wherein the cytotoxic agent partitions out once the substrate-agent conjugate is acted upon by the enzyme component of the targeted antibody-enzyme conjugate, so that the agent then accretes at the target site to a significantly greater extent than the substrate-agent conjugate would accrete in the absence of the enzyme, said polymer substrate-agent conjugate comprising a polymer substrate for said enzyme, wherein either (1) a plurality of molecules of said agent are linked to said polymer substrate, or (2) said polymer substrate is a coating on the agent, which agent is one that is attracted to the target site in the absence of such coating, such that cleavage by the enzyme liberates the agent;
   wherein said enzyme is selected from the group consisting of dextranase, cellulase and beta-glucosidase.

2. The method of claim 1, wherein in step (b), said enzyme is injected after a sufficient time for said bispecific antibody or antibody fragment to localize at said site and for unbound bispecific antibody or antibody fragment to substantially clear from the circulation of said mammal.

3. The method of claim 1, wherein said antibody or antibody fragment in said antibody-enzyme conjugate specifically binds to an antigen produced by or associated with a member selected from the group consisting of a tumor, an infectious lesion, a parasitic lesion, a fibrin clot, a myocardial infarction, an atherosclerotic plaque, a non-cancerous cell that has an antigen that enables targeting of said non-cancerous cell by said antibody-enzyme conjugate and a damage-related site of a damaged, non-cancerous cell.

4. The method of claim 1, wherein said enzyme is a dextranase or a cellulase, and wherein said polymer substrate-agent conjugate comprises said agent conjugated to (1) at least one solubilizing dextran or carboxymethyl-cellulose oligomer which is a polymer substrate for said enzyme and (2) a non-substrate aminodextran or a polylysine carrier.

5. The method of claim 1, wherein said mammal is a human.

6. A sterile injectable preparation, for targeting a cytotoxic agent to a target site, comprising;
   (a) a first sterile injectable solution containing an effective amount for targeting of a bispecific antibody or antibody fragment having a first binding site specific for an antigen present at a target site and a second binding site specific for an epitope of an enzyme, wherein binding to said epitope does not interfere with enzyme activity, said antibody or antibody fragment being dissolved in a pharmaceutically acceptable sterile injection vehicle;
   (b) a second sterile injectable solution containing an effective amount for enzyme activity at said target site of said enzyme, said enzyme being dissolved in a pharmaceutically acceptable sterile injection vehicle; and
   (c) a third sterile injectable solution containing an effective amount, for deposition at said site, of a serum soluble polymer substrate-agent conjugate which is capable of transformation by said enzyme to form a product comprising at least one cytotoxic agent that is relatively insoluble in serum in vivo, said polymer substrate-agent conjugate comprising a polymer substrate for said enzyme, wherein either (1) a plurality of molecules of said agent are linked to said polymer substrate, or (2) said polymer substrate is a coating on the agent, which agent is one that is attracted to the target site in the absence of such coating, such that cleavage by the enzyme liberates the agent, said polymer substrate-agent conjugate being dissolved in a pharmaceutically acceptable sterile injection vehicle; wherein said enzyme is selected from the group consisting of dextranase, cellulase, and beta-glucosidase.

7. A kit, for targeting a cytotoxic agent to a target site, comprising;
(a) a first sterile container containing an effective amount for targeting of a bispecific antibody or antibody fragment having a first binding site specific for an antigen present at a target site and a second binding site specific for an epitope of an enzyme which does not interfere with enzyme activity;
(b) a second sterile container containing an effective amount for enzyme activity at said target site of said enzyme; and
(c) a third sterile container containing an effective amount for deposition at said site of a serum soluble polymer substrate-agent conjugate which is capable of transformation by said enzyme to form a product comprising a cytotoxic agent that is relatively insoluble in serum in vivo, said polymer substrate-agent conjugate comprising a polymer substrate for said enzyme, wherein either (1) a plurality of molecules of said agent are linked to said polymer substrate, or (2) said polymer substrate is a coating on the agent, which agent is one that is attracted to the target site in the absence of such coating, such that cleavage by the enzyme liberates the agent;
wherein said enzyme is selected from the group consisting of dextranase, cellulase, and beta-glucosidase.

8. A method as claimed in claim 1, wherein said polymer substrate is a dextran and said enzyme is dextranase.

9. A method as claimed in claim 1, wherein said polymer substrate is aminodextran and said enzyme is dextranase.

10. A method as claimed in claim 9, wherein said agent is linked to amino groups of said aminodextran.

11. A method as claimed in claim 10, wherein said cytotoxic agent is a drug that is loaded onto said amino dextran in a ratio of monosaccharide subunits to drug of from about 3 to about 25.

12. The method as claimed in claim 1, wherein said polymer substrate is a carboxymethylcellulose which comprises functional groups to which said cytotoxic agent is linked and wherein said enzyme is cellulase.

13. A method as claimed in claim 9, wherein said agent is linked to functional groups of a carboxymethylcellulose.

14. A method as claimed in claim 1, wherein said polymer substrate-agent conjugate comprises a cytotoxic agent, wherein the cytotoxicity of cytotoxic agent is reduced by conversion to a conjugate with said polymer substrate.

15. A method as claimed in claim 1, wherein said plurality of molecules of said agent are linked to the backbone of said polymer substrate.

16. A method as claimed in claim 1, wherein said plurality of molecules of said agent are linked to oligomers that are substrates for the enzyme, and said oligomers are linked to the backbone of a polymer substrate.

17. A method as claimed in claim 1, wherein said polymer substrate is a coating on an agent that is attracted to a target in the absence of such coating.

18. A method as claimed in claim 17, wherein said substrate-agent conjugate comprises a carrier conjugate of a carrier polymer that bears said cytotoxic agent, and said carrier conjugate is condensed with a plurality of oligomers that are substrate for said enzyme, such that said carrier conjugate is released by action of said enzyme on said oligomers at the target site.

19. A method for targeting a cytotoxic agent to a target site, comprising the steps of:
(a) injecting a mammal parenterally with an effective amount for targeting of a bispecific antibody or antibody fragment having a first binding site specific for an antigen present at a target site and a second binding site specific for an epitope on an enzyme, wherein binding to said epitope does not interfere with enzyme activity;
(b) subsequently injecting said mammal parenterally with an effective amount for enzyme activity of said enzyme, such that said bispecific antibody or antibody fragment binds said enzyme to form an antibody-enzyme conjugate in situ; and
(c) after a sufficient period of time for localization of said antibody-enzyme conjugate at the target site and for unbound antibody-enzyme conjugate to clear from the circulatory system of the mammal, further injecting said mammal parenterally with an effective amount for deposition at said site of a serum soluble substrate-agent conjugate which is capable of transformation by said enzyme to form a product comprising a cytotoxic agent that is relatively insoluble in serum in vivo, wherein the cytotoxic agent partitions out once the substrate-agent conjugate is acted upon by the enzyme component of the targeted antibody-enzyme conjugate, so that the agent then accretes at the target site to a significantly greater extent than the substrate-agent conjugate would accrete in the absence of the enzyme;
wherein said enzyme is glucuronidase.

20. A sterile injectable preparation, for targeting a cytotoxic agent to a target site, comprising;
(a) a first sterile injectable solution containing an effective amount for targeting of a bispecific antibody or antibody fragment having a first binding site specific for an antigen present at a target site and a second binding site specific for an epitope of an enzyme, wherein binding to said epitope does not interfere with enzyme activity, said antibody or antibody fragment being dissolved in a pharmaceutically acceptable sterile injection vehicle;
(b) a second sterile injectable solution containing an effective amount for enzyme activity at said target site of said enzyme, said enzyme being dissolved in a pharmaceutically acceptable sterile injection vehicle; and
(c) a third sterile injectable solution containing an effective amount, for deposition at said site, of a serum soluble substrate-agent conjugate which is capable of transformation by said enzyme to form a product comprising at least one cytotoxic agent that is relatively insoluble in serum in vivo, said substrate-agent conjugate comprising a substrate for said enzyme, wherein cleavage by the enzyme liberates serum soluble cytotoxic agent in situ, said substrate-agent conjugate being dissolved in a pharmaceutically acceptable sterile injection vehicle;
wherein said enzyme is glucuronidase.

21. A kit for targeting a cytotoxic agent to a target site, comprising;
(a) a first sterile container containing an effective amount for targeting of a bispecific antibody or antibody fragment having a first binding site specific for an antigen present at a target site and a second binding site specific for an epitope of an enzyme which does not interfere with enzyme activity;

(b) a second sterile container containing an effective amount for enzyme activity at said target site of said enzyme; and (c) a third sterile container containing an effective amount for deposition at said site of a soluble substrate-agent conjugate which is capable of transformation by said enzyme to form a product comprising a cytotoxic agent, said substrate-agent conjugate comprising a substrate for said enzyme, wherein cleavage by the enzyme liberates soluble cytotoxic agent in situ, wherein said enzyme is glucuronidase.

22. A method according to claim 1, wherein said polymer substrate is a coating on the agent, which agent is one that is attracted to the target site in the absence of such coating, such that cleavage by the enzyme liberates the agent.

23. A preparation according to claim 6, wherein said polymer substrate is a coating on the agent, which agent is one that is attracted to the target site in the absence of such coating, such that cleavage by the enzyme liberates the agent.

24. A kit according to claim 7, wherein said polymer substrate is a coating on the agent, which agent is one that is attracted to the target site in the absence of such coating, such that cleavage by the enzyme liberates the agent.

25. The method of claim 1, wherein said cytotoxic agent is at least one boron addend, drug, toxin, radioisotope, vasodilator, cytokine, radiosensitizer or photosensitizer.

26. The kit of claim 7, wherein said cytotoxic agent is at least one boron addend, drug, toxin, radioisotope, vasodilator, cytokine, radiosensitizer or photosensitizer.

* * * * *